United States Patent
Hess et al.

(10) Patent No.: US 6,592,604 B2
(45) Date of Patent: Jul. 15, 2003

(54) VESSEL HARVESTING RETRACTOR WITH DISSECTION ELEMENT

(75) Inventors: Christopher J. Hess, Lebanon, OH (US); Michael F. Clem, Maineville, OH (US); Gary W. Knight, West Chester, OH (US); Rudolph H. Nobis, Mason, OH (US); Dale R. Schulze, Lebanon, OH (US); Kristin L. Jambor, Cincinnati, OH (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/967,200

(22) Filed: Sep. 28, 2001

(65) Prior Publication Data

US 2003/0065351 A1 Apr. 3, 2003

(51) Int. Cl.[7] ............................................... A61B 17/00
(52) U.S. Cl. ..................................................... 606/190
(58) Field of Search ............................... 606/190, 191, 606/192, 108–159; 600/201–213, 235

(56) References Cited

U.S. PATENT DOCUMENTS

| | | |
|---|---|---|
| 5,591,183 A | 1/1997 | Chin |
| 5,593,418 A | 1/1997 | Mollenauer |
| 5,601,581 A | 2/1997 | Fogarty et al. |
| 5,667,480 A | 9/1997 | Knight et al. |
| 5,695,514 A | 12/1997 | Chin |
| 5,722,934 A | 3/1998 | Knight et al. |
| 5,725,479 A | 3/1998 | Knight et al. |
| 5,730,748 A | 3/1998 | Fogarty et al. |
| 5,797,947 A | 8/1998 | Mollenauer |
| 5,817,013 A | 10/1998 | Ginn et al. |
| 5,836,945 A | 11/1998 | Perkins |
| 5,853,417 A | 12/1998 | Fogarty et al. |
| RE36,043 E | 1/1999 | Knighton |
| 5,873,889 A | 2/1999 | Chin |
| 5,876,413 A | 3/1999 | Fogarty et al. |
| 5,891,140 A | 4/1999 | Ginn et al. |
| 5,899,913 A | 5/1999 | Fogarty et al. |
| 5,902,316 A | 5/1999 | Mollenauer |
| 5,916,233 A | 6/1999 | Chin |
| 5,922,004 A | 7/1999 | DuBois |
| 5,928,135 A | 7/1999 | Knight et al. |
| 5,938,680 A | 8/1999 | Ginn |
| 5,968,065 A | 10/1999 | Chin |
| 5,968,066 A | 10/1999 | Fogarty et al. |
| 5,970,982 A | 10/1999 | Perkins |
| 5,972,010 A | 10/1999 | Taheri |
| 5,976,168 A | 11/1999 | Chin |
| 5,980,549 A | 11/1999 | Chin |
| 5,984,937 A | 11/1999 | Morse et al. |
| 6,019,771 A | 2/2000 | Bennett et al. |
| 6,022,313 A | 2/2000 | Ginn et al. |
| 6,036,713 A | 3/2000 | Kieturakis |
| 6,036,714 A | 3/2000 | Chin |
| 6,042,538 A | 3/2000 | Puskas |
| 6,059,802 A | 5/2000 | Ginn |
| 6,068,639 A | 5/2000 | Fogarty et al. |
| 6,071,232 A | 6/2000 | Knighton et al. |
| 6,120,434 A | 9/2000 | Kimura et al. |
| 6,139,489 A | 10/2000 | Wampler et al. |
| 6,193,653 B1 * | 2/2001 | Evans et al. ................. 600/210 |

FOREIGN PATENT DOCUMENTS

| | | |
|---|---|---|
| EP | 0 979 635 A2 | 2/2000 |
| WO | WO 99/66842 | 12/1999 |
| WO | WO 00/15116 | 3/2000 |

* cited by examiner

Primary Examiner—Michael J. Milano
Assistant Examiner—(Jackie)Tan-Uyen T. Ho

(57) ABSTRACT

A surgical instrument for dissecting a vessel in a patient. The surgical instrument includes a spoon retractor having a proximal end and a distal end, said spoon retractor defining a working space in the tissue of a patient, a dissecting element proximate to the spoon retractor for dissecting tissue from a vessel, and a handle for manipulating the spoon retractor near the vessel. Also provided is a method for dissecting a vessel including the steps of providing the surgical instrument for dissecting a vessel in a patient described above. Making an incision in a patient. Inserting the spoon retractor into the incision. Creating a working space in the tissue of the patient near the vessel being dissected, and manipulating the dissecting element to further dissect tissue surrounding the vessel being dissected.

11 Claims, 5 Drawing Sheets

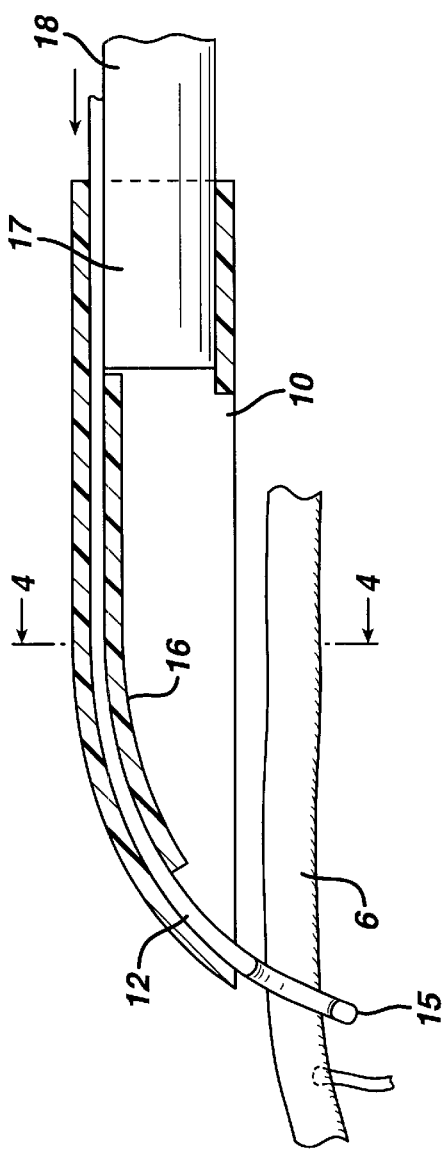
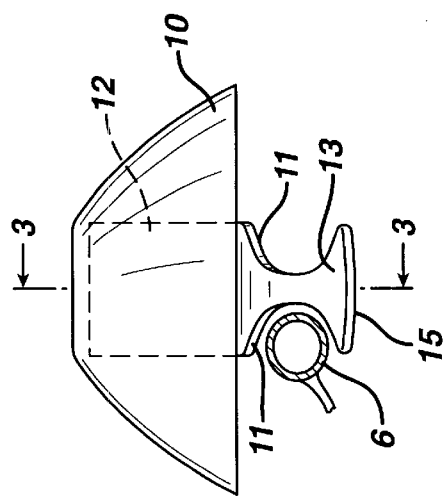
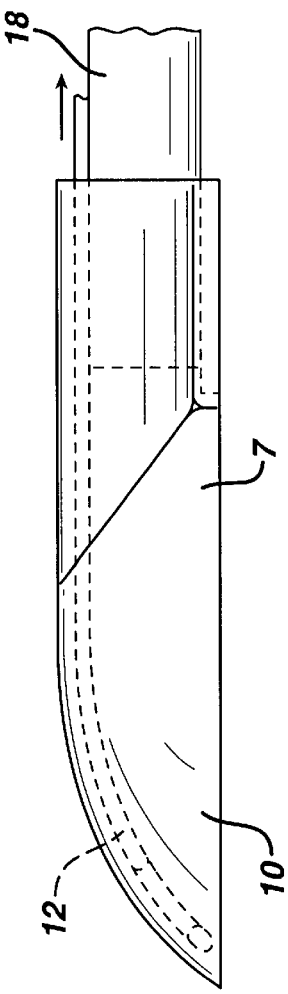
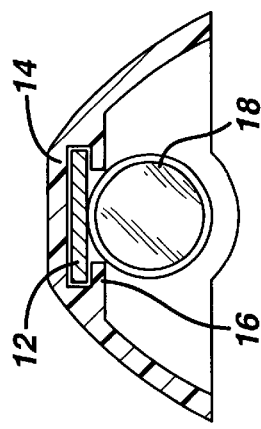

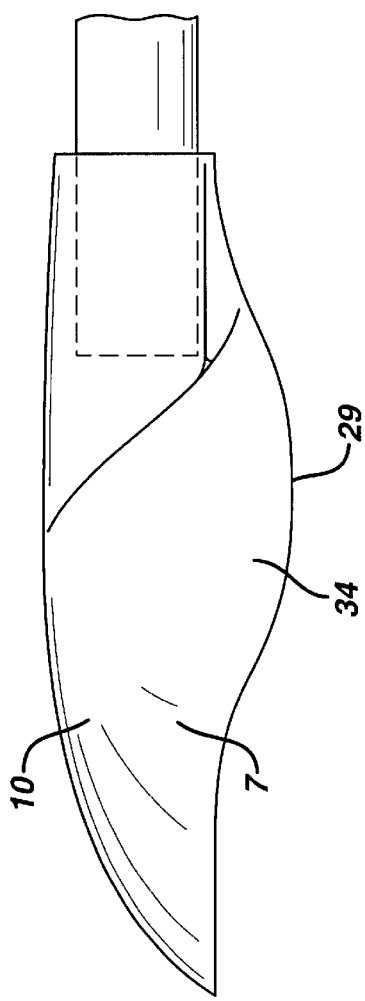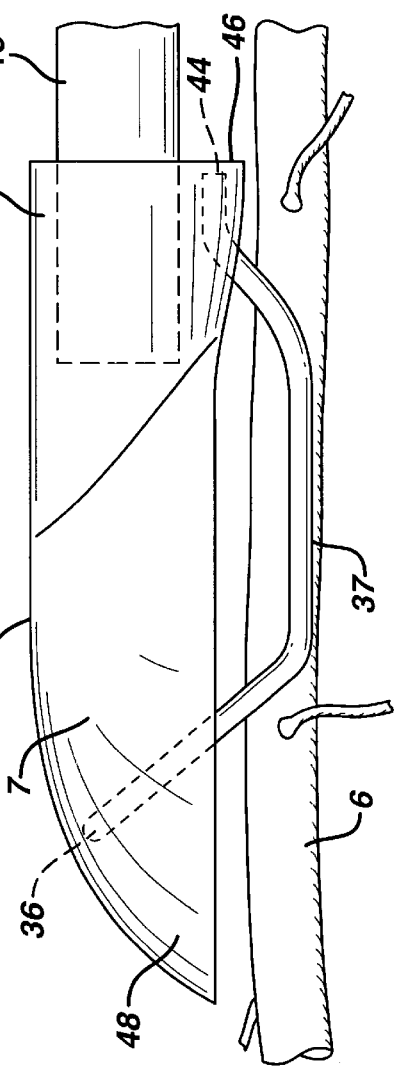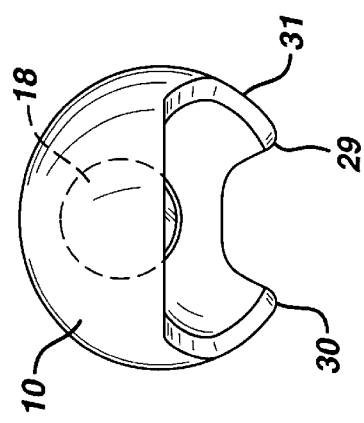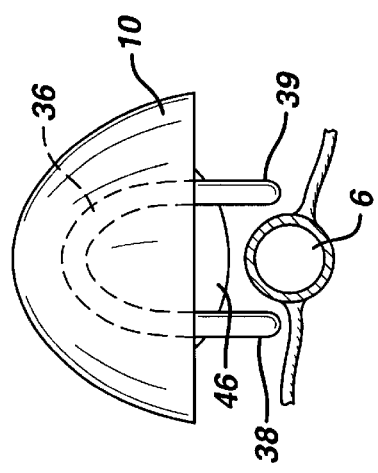

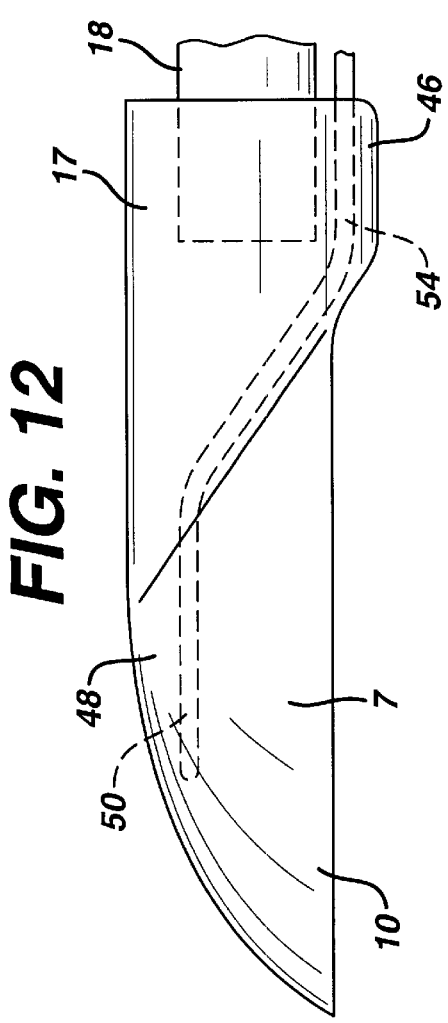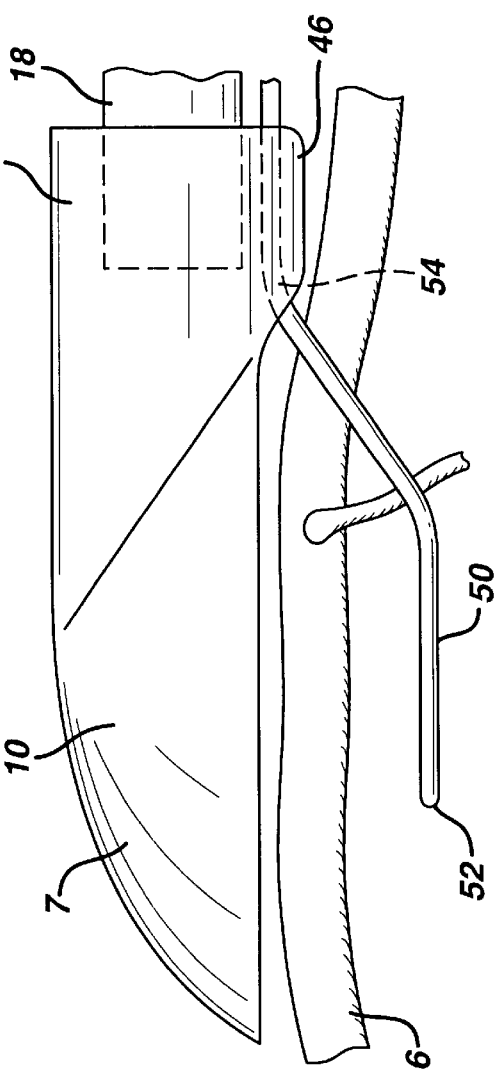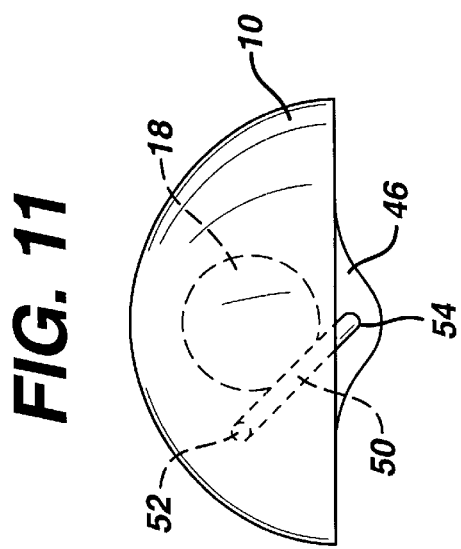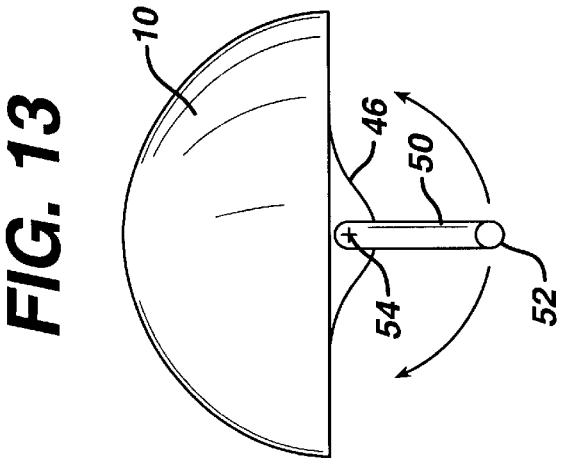

VESSEL HARVESTING RETRACTOR WITH DISSECTION ELEMENT

FIELD OF THE INVENTION

This invention relates to surgical devices and methods for dissecting around elongated tissue structures. In particular, this invention relates to devices and methods for dissecting around a blood vessel such as a saphenous vein during an endoscopic vessel harvesting procedure.

BACKGROUND OF THE INVENTION

Endoscopic vein harvesting (EVH), particularly of the greater saphenous vein in the leg, is a surgical procedure for obtaining a graft vessel for a coronary artery bypass graft (CABG) procedure. A physician's assistant (PA) typically performs the EVH on one or both legs of the patient while a cardiac surgeon operates on the patient's chest in preparation for the grafts. Performing the EVH in a timely manner is important so that the PA can present the prepped vessel to the surgeon by the time the surgeon is ready to attach the graft vessel to the heart. The EVH procedure learning curve and additional time required to harvest a blood vessel using minimally invasive techniques continue to be issues for the rapid adoption of the procedure. The present invention improves the ease of use and decreases the time required to harvest a vessel. Specifically, this invention reduces the number of instrument exchanges through the surgical incision in the patient.

Several investigators have proposed devices and methods for performing EVH, as disclosed in the patents cited. For example, U.S. Pat. No. 5,928,138 ("Method and Devices for Endoscopic Vessel Harvesting", assigned to Ethicon Endo-Surgery, Inc., and issued on Jul. 27, 1999) discloses an optical dissector having a concave working head. A commercial version of this optical dissector is called the Clear-Glide subcutaneous retractor and is available from Ethicon, Inc., Somerville, N.J. The ClearGlide is currently one of the main products available today for performing EVH, and provides good access and visibility to the surgical site along the greater saphenous vein.

The PA normally uses the ClearGlide with other endoscopic, surgical dissection instruments in order to isolate the vessel from surrounding tissues. The PA introduces these instruments through a channel provided in the handle and shaft of the ClearGlide in order to operate on tissues within a working space created by a concave working head.

Known methods and devices for performing vessel dissection are discussed in detail in U.S. Pat. Nos. 5,667,480 issued Sep. 16, 1997 and 5,722,934 issued Mar. 3, 1998, both issued to Knight, et al, both of which are incorporated herein by their reference.

Of the known devices and methods for dissection of tissues there remains one constant problem. The problem is that to perform the dissection, extra tools must be inserted along the guide rails of the device through the original incision. Often times this means that to perform a single dissection of a vessel multiple tools must be inserted in succession into the body. Additionally, the harvesting device remains in the body throughout the procedure.

This requirement of inserting the tools in succession and exchanging one tool for another to perform each step of the operation requires extra time, this in turn can be a drain on the individual surgeons resources. Further, because of this increased amount of time, which the surgeon requires to perform the operation, the stress on the patient is increased. Minimization of patient stress is naturally a concern during any surgical procedure. Therefore, the elimination of some or all of the time extending tool exchanges would greatly benefit not only the patient but the surgeon as well.

What is needed, therefore, is a surgical instrument having a concave working head for creating a working space near the vessel to be harvested, and that has at least one dissection element connected to the concave working head. An operator may use the dissection element for dissecting around all sides of the vessel so that it is less necessary to use other dissection instruments. The operator may also use the dissecting element for supporting a tissue structure such as a side branch while it is operated on by another surgical instrument, such as a surgical scissors, ligation instrument, or the like.

SUMMARY OF THE INVENTION

The present invention is directed to solving the shortcomings of known vessel retractors, by providing a superior vessel retractor, promoting efficient dissection of vessels, and limiting the stress on patients. The objects of the present invention are the minimization of the tool exchanges, increased efficiency of operation, minimization of patient stress, and increased ease of the overall harvest operation. Further, the present invention pertains to a vessel retractor having a dissecting element. The surgical instrument comprises a spoon retractor having a proximal end and a distal end, said spoon retractor defining a working space in the tissue of a patient, a dissecting element proximate to said spoon retractor for dissecting tissue from a vessel, and means for manipulating said spoon retractor near the vessel. The means for introducing and manipulating the spoon retractor near the vessel comprises, a shaft having a distal end and a proximal end, the distal end of the shaft connected to the proximal end of the spoon retractor, the shaft having a lumen in communication with the working space for insertion of an endoscope there through and a handle connected to a proximal end of the shaft for manipulation of the spoon retractor connected thereto.

The dissecting element may be rigidly fastened to the spoon retractor. In such a configuration the dissecting element comprises a wireform, the wireform comprises a left side rail and a right side rail rigidly connected to the spoon retractor at a proximal end of the wireform, said left and right side rails being connected to each other at a distal end of the wireform and dissecting tissue from the left and right surfaces of the vessel. Additionally the wireform may project upward in the direction of the spoon retractor, and form a U-shape at the distal end of the wireform to facilitate placement of the vessel between the left and right side rails.

The surgical instrument may comprise a control for controlling the dissecting element, when the dissecting element movably connects to the spoon retractor and moves relative to said spoon retractor upon actuation of the control, to facilitate dissection of tissue from the vessel. In such a configuration the dissecting element comprises a movable arm having an extended portion and a shank, the movable arm being rotatable about an axis defined by the shank.

In another configuration the dissection element may comprise a flexible arm slidably retained in said spoon retractor, and movable between an extended position and a retracted position. In such a configuration the distal end of the flexible arm defines at least one curved portion, the curved portion further defining an arm which extends to an outer edge of the flexible arm and facilitating the dissection of tissue from the vessel. The flexible arm is prevented from entering the workspace by guide rails.

Also provided is a method for dissecting a vessel comprising the steps of: providing a surgical instrument for dissecting a vessel in a patient; said surgical instrument comprising a spoon retractor having a proximal end and a distal end; said spoon retractor defining a working space in the tissue of the patient near the vessel to be dissected; a dissecting element proximate to said spoon retractor for dissecting tissue from a vessel; and a means for manipulating said spoon retractor near the vessel, making an incision in a patient; inserting said spoon retractor into the incision; creating a working space in the tissue of the patient near the vessel being dissected; and manipulating said dissecting element to further dissect tissue surrounding the vessel being dissected.

The method further comprises the step of providing a surgical instrument for dissecting a vessel comprising a wireform rigidly attached to the spoon retractor, the wireform comprising a left side rail and a right side rail rigidly connected to the spoon retractor at a proximal end of the wireform, said left and right sides being connected to each other at a distal end of the wireform.

Preferably the manipulating step comprises sliding the wireform along the vessel while the left and rights sides are laterally disposed on the left and right sides of the vessel respectively.

In a configuration where the dissecting element is movably connected to the spoon retractor, the manipulating step may comprise moving the dissecting element relative to said spoon retractor upon actuation of a control.

In a configuration where said dissecting element is a movable arm having an extended portion and a shank, the manipulation may comprise rotating the movable arm about an axis defined by the shank, wherein said manipulating step further comprises sliding the spoon retractor and attached the dissection element along the vessel, and rotating the movable arm about the vessel to dissect the vessel from the surrounding tissue.

The method for dissecting may also comprise using a dissecting element comprising a flexible arm slidably retained in said spoon retractor, and movable between an extended position and a retracted position. Wherein the distal end of the flexible arm defines at least one curved portion, the curved portion further defining an arm which extends to an outer edge of the flexible arm.

In such a configuration the manipulating step preferably comprises, extending the flexible arm from the retracted to the extended position, and sliding the spoon retractor and attached dissection element along the vessel, wherein the curved portion of the flexible arm is placed on at least one side of the vessel to dissect the vessel from the surrounding tissue.

BRIEF SUMMARY OF THE DRAWINGS

FIG. 2 is a front view of a spoon retractor of the surgical instrument of FIG. 1, the spoon retractor having a flexible arm as a dissecting element in an extended position;

FIG. 3 is a side sectional view of the spoon retractor shown in FIG. 2 taken along line 3—3;

FIG. 4 is a sectional view of the spoon retractor shown in FIG. 3 taken along line 4—4;

FIG. 5 is a side view of the spoon retractor shown in FIG. 3 in a retracted position;

FIG. 7 is a front view of a first variation of the spoon retractor of the present invention with curved edges as a dissecting element;

FIG. 8 is a side view of the spoon retractor shown in FIG. 7;

FIG. 9 is a front view of a second variation of the spoon retractor of the present invention with fixed rails as a dissecting element;

FIG. 10 is a side view of the spoon retractor shown in FIG. 9;

FIG. 11 is a front view of a third variation of the spoon retractor of the present invention with a movable arm as a dissecting element in a retracted position;

FIG. 12 is a side view of the spoon-retractor shown in FIG. 11;

FIG. 13 is a front view of the spoon retractor shown in FIG. 11 in an extended position; and FIG. 14 is a side view of the spoon retractor shown in FIG. 13 in an extended position.

DETAILED DESCRIPTION OF THE INVENTION

A surgical instrument for endoscopic dissection of vessels for CABG surgery as known in the art generally comprises a concave working head, a shaft, and a handle. The instrument is typically fitted with an endoscope inserted through a handle and the shaft so that an operator may view into a working space created by concave working head.

In operation the surgeon introduces the concave working head and a portion of shaft through a surgical incision and manipulates surgical instrument alongside the saphenous vein in order to free the vein from surrounding tissues and to isolate side branches of the vein that must be ligated prior to removal of the vein from the patient's leg.

The concave working head may be made from a clear plastic so that the operator may visualize tissue structures adjacent to it as well as inside the working space. U.S. Pat. No. 5,928,138 also discloses how surgical instrument may be used with other surgical instruments for dissecting and harvesting a vein. The present invention reduces the time required to perform the EVH procedure (and subsequent trauma to tissue) due to fewer exchanges of these additional instruments into incision.

Figure 1:
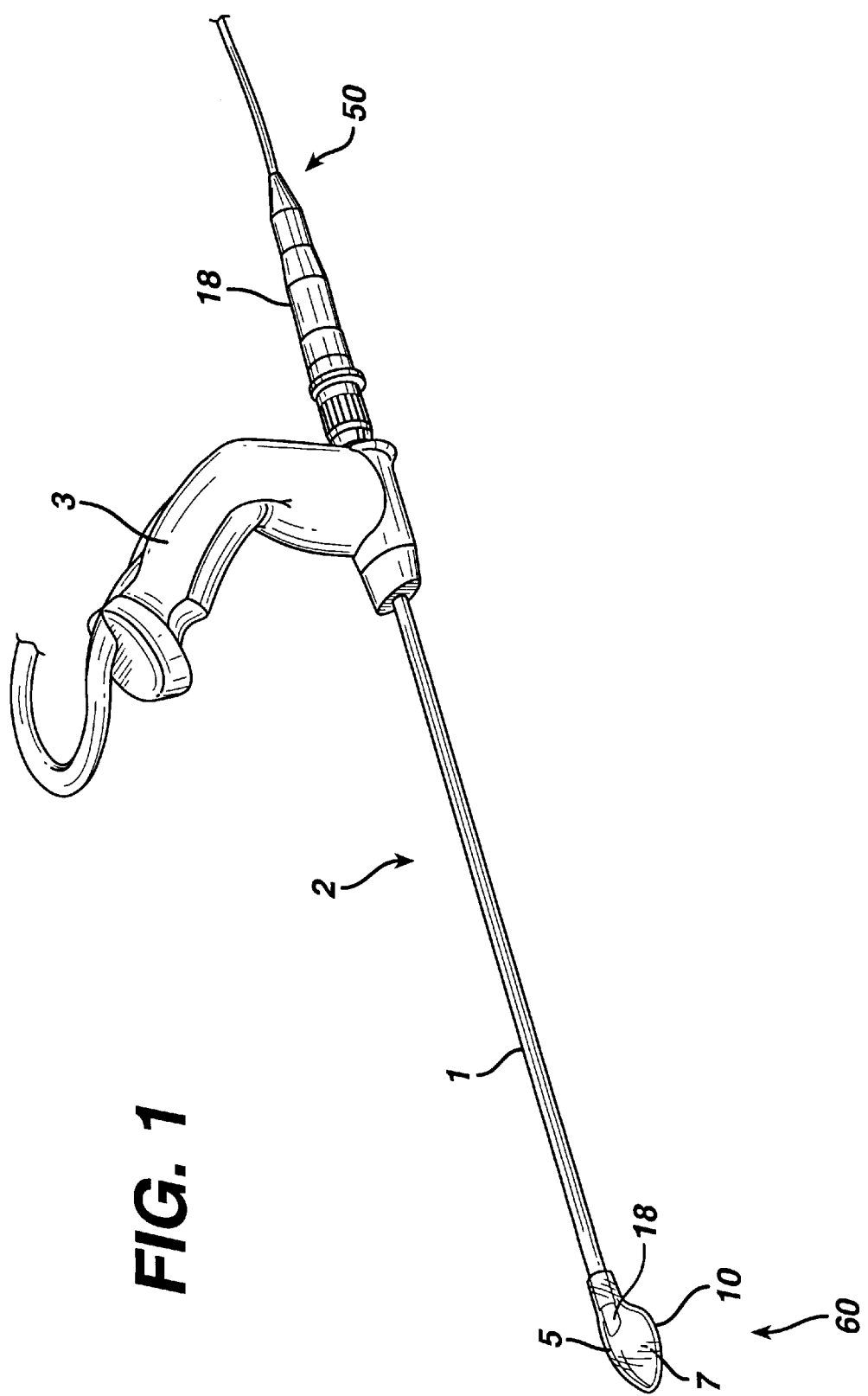
FIG. 1 is a perspective view of a preferred implementation of a surgical instrument of the present invention, used for dissecting and harvesting a vein.

Referring now to FIG. 1, a surgical instrument is illustrated therein generally referred to by reference number 2. The present invention includes at least one dissecting element (shown in FIGS. 2–14), which is either movably connected or fixed to a concave working head, also referred to as a spoon retractor 10. The spoon retractor 10 is useful for dissection of tissue such as is required for separating the saphenous vein from surrounding tissues during an EVH. Surgical instrument 2 may be used with an endoscope 18 in order to view inside the working space. In the descriptions that follow, several variations of the spoon retractor 10 and dissecting elements are described. For the embodiments shown, the spoon retractor 10 is preferably attached to an elongated shaft 1 and a handle 3, similar to the surgical instrument of the prior art.

FIG. 2 is a front view and FIG. 3 is a side sectional view of a spoon retractor 10 of the present invention. Spoon retractor 10 is an improvement of concave working head of the prior art. In this implementation, spoon retractor 10 is symmetrically shaped with a proximal end 17 attached to the distal end of a shaft 1. Spoon retractor 10 tapers to a distal end 19 so that an operator 4 may easily use spoon retractor 10 to separate tissue layers and isolate a vein 6 from surrounding tissues. Spoon retractor 10 is preferably made of a medical grade, injection moldable plastic such as polycarbonate and is optionally clear for endoscopic viewing of tissue both inside the working space and adjacent to spoon retractor 10. In the implementation of FIGS. 2 and 3, spoon retractor 10 includes a retractable, flexible arm 12. An upper layer 14 and a lower layer 16 of spoon retractor 10 define a channel that extends partially between distal end 19 and proximal end 17, and slidably retains flexible arm 12. An operator 4 may position flexible arm 12 at an extended position such as shown in FIGS. 2 and 3, at a retracted position, as shown in FIGS. 4 and 5, or at any position between the extended and retracted positions. A control (not shown) for moving flexible arm 12 is preferably located on a portion of the surgical instrument 2 that remains external to the patient during the procedure, such as on the proximal end 50 of shaft 1 or on handle 3, as may be easily envisioned by those skilled in the art.

In the retracted position, the flexible arm 12 lies above the level of the endoscope 18, and portions which are located outside of the spoon retractor 10 may lie on the shaft 1. Flexible arm 12 may be made of a medical grade, injection moldable plastic such as high-density polyethylene. A distal end of flexible arm 12 comprises two opposing curved portions 11 for a traumatically sliding along the sides of an elongate tissue structure such as a vein 6 in order to free the vein 6 from surrounding tissues. Curved portions 11 define an arm 13 that extends distally to an outer edge 15 to assist in separating the vein 6 from the connecting tissues.

Figure 6:
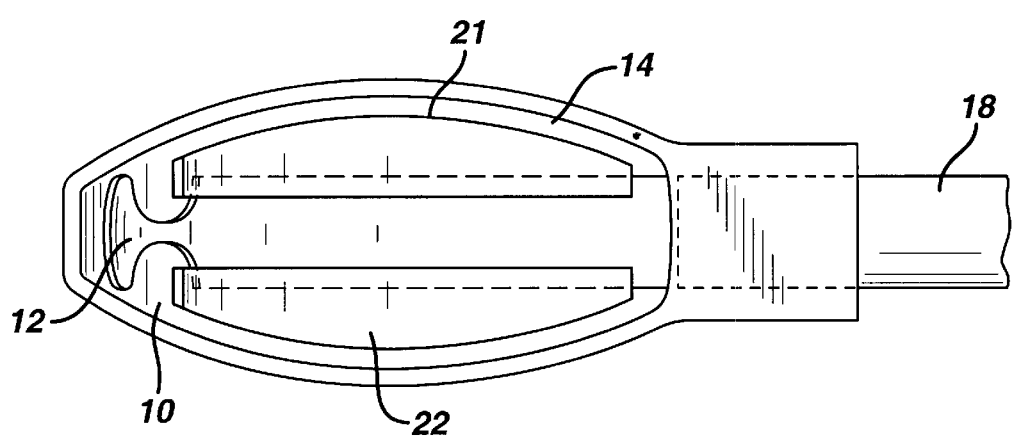
FIG. 6 is a bottom view of the spoon retractor shown in FIG. 5 in the retracted position.

FIG. 6 shows a bottom view of spoon retractor 10 and corresponds with FIGS. 4 and 5 for when flexible arm 12 is in the retracted position. Lower layer 16 (see FIG. 3) comprises two guide rails 22 to support flexible arm 12. Guide rails 22 connect to an inside surface of spoon retractor 10. The guide rails 22 also serve to insure that the flexible arm 12 does not restrict the field of view of the endoscope 18.

FIGS. 7 and 8 are a front view and a side view of a first variation of a spoon retractor 10, respectively, with a left curved edge 30 and an opposing right curved edge 31 extending from a bottom edge 29 on each side of spoon retractor 10. In this implementation, a left middle section (not shown) and a right middle section 34 blends with the curvation on each side of spoon retractor 10. As can be seen in FIG. 7, left curved edge 30, right curved edge 31 and spoon retractor 10 approximately surround the longitudinal axis of spoon retractor 10, thus allowing an operator to place spoon retractor 10 near a vessel with left curved edge 30 and right curved edge 31 on opposing sides of the vessel. The operator 4 may then slide spoon retractor 10 back and forth along the vessel to free the vessel from surrounding tissue.

FIGS. 9 and 10 show a second variation of the spoon retractor 10 of the present invention. FIG. 9 is a front view and FIG. 10 is a side view, showing a wireform dissecting element 37 comprising a left side rail 38 and a right side rail 39 fixed to spoon retractor 10. Wireform dissecting element 37 preferably has a curved distal end 36 joining left side rail 38 and right side rail 39. Wireform dissecting element 37 further comprises a pair of proximal ends 44, which are fixedly connected to spoon retractor 10. Cavity 48 of spoon retractor 10 retains and supports curved distal end 36. Wireform dissecting element 37 is made from a medical grade material such as stainless steel wire having a diameter approximately in the range of one to two millimeters. The operator 4 may position left side rail 38 and right side rail 39 and on either side of a vessel and move spoon retractor 10 slowly forward and back to separate vein 6 from the connecting tissue layers.

FIGS. 11–14 show a third variation of the spoon retractor 10 of the present invention. FIGS. 11 and 12 show front and side views, respectively, of spoon retractor 10, and include a movable arm 50 shown in a first position. An extended portion 46 at a proximal end 42 of the spoon retractor 10 rotatably retains a shank 54 of movable arm 50. An operator 4 moves movable arm 50 between the retracted first position and a second position (FIGS. 11 and 13, respectively) by actuating a rotation control (not shown) preferably located on the proximal end of shaft 1 or on handle 3 (see FIG. 1). Actuation of a distal element of a surgical element by a control rod is well known in the art.

Movable arm 50 includes a tip 52 for dissecting tissues. Shank 54 preferably lies directly below endoscope 18. Movable arm 50 is preferably made from a stainless steel wire having a diameter approximately in the range of one to two millimeters. Movable arm 50 may rotate in either direction about the axis defined by the shank and may also rotate a full 360 degrees.

The operation of the surgical instrument 2 of the present invention will now be discussed with reference to the figures. The surgical instrument 2 of the present invention has a particular ability in dissecting vessels from tissue in a patient however, such a use is given by way of example only and does not limit the scope or spirit of the present invention.

Once a device comprising at least one of the dissection elements discussed above is provided, the surgeon determines the location of the vessel to be dissected, and makes an incision in the patient. The spoon retractor is inserted into the incision and blunt dissection of the tissue surrounding the vessel 6 is performed. For extraction purposes, it is preferable to dissect as much tissue from the vessel as possible. The initial insertion of the spoon retractor 10 creates a working space 7 in the tissue of the patient near the vessel 6 being dissected. This working space provides a location where the operator may utilize the various dissection elements, discussed above to dissection the vessel from the surrounding tissue. Finally the dissection elements need to be manipulated by the user to further dissect tissue surrounding the vessel 6 being dissected.

The dissection of the vessel 6 is accomplished by moving the spoon retractor 10 along the vessel and separating the tissue from the vessel. To assist in the dissection there are various forms of dissection elements which can be provided, as discussed above. Each of the various dissection elements can be incorporated into the method described here with some variation of the manipulation step.

One of the dissection elements which may be provided is shown in FIGS. 7 and 8. The dissection element comprises the spoon retractor 10 having curved edges 30, 31 extending from the bottom edge on each side of the spoon retractor. The dissection element is used by orienting the vessel 6 between the two curved edges 31. Once the vessel is so oriented the spoon retractor 10 is moved along the vessel 6. This movement causes the curved edges 30, 31 to dissect the vessel from the tissue located on either side.

Another dissection element provided comprises a rigidly attached wireform 37 having left and right side rails 38, 39, and these rails are connected at the distal end of the wireform 37. Such a dissection element 37 is used by orienting the left side rail 38, on a first side of the vessel 6, and the right side rail 39 on a second side of the vessel 6. The vessel is captured by the wireform by operation of the U-Shape connection point of the dissection element. After the vessel 6 is captured, the spoon retractor 10 and wireform 37 are slid along the length of the vessel. The left side rail dissecting on the first side of the vessel and the right side rail dissecting the right side of the vessel. The U-shaped connection assists in the dissection of tissue on the top surface of the vessel.

Yet another dissection provided is one having a movable arm 50 having an extended portion and a shank 44 as shown in FIGS. 11–14. The dissecting element is movably connected to the spoon retractor 10, and the manipulation comprises rotating the movable arm 50 about an axis defined by the shank 44. Sliding the spoon retractor 10 and attached movable arm 50 along the vessel, and simultaneously rotating the movable arm 50 about the vessel tissue, dissects on all sides of the vessel from the surrounding tissue.

Additionally, when the movable arm 50 is in the position shown in FIG. 14, the dissection element can slidingly engage the tissue along the axis defined by the shank to dissect it from the vessel. The movable arm 50 can be forced along one side of the vessel 6 while the spoon retractor 10 is moved along another surface of the vessel 6. Upon projecting the spoon retractor a certain distance, the movable arm can be rotated to dissect tissue from the vessel by the circumferential movement of the movable arm around the vessel 6.

Still another dissection element provided is one having a flexible arm 12 slidably retained in said spoon retractor, and movable between an extended position and a retracted position, as shown in FIGS. 2–8. The distal end of the flexible arm 12 defines at least one curved portion 11. The curved portion 11 further defining an arm 13 which extends to an outer edge of the flexible arm 12. This dissection element is manipulated by extending the flexible arm from the retracted to the extended position, and sliding the spoon retractor 10 and attached flexible arm 12 along the vessel 6, at the same time the curved portion 11 of the flexible arm 12 is placed on at least one side of the vessel 6 to dissect the vessel 6 from the surrounding tissue. Typically, the flexible arm 12 has two curved portions 11 and will be used to dissect the tissue from one side of the vessel 6 and then a second side of the vessel 6. During the dissection the curved portion 11 slides along the surface of the vessel 6. The arm 13 facilitates the dissection on the underside of the vessel 6.

Those skilled in the art will appreciate that the methods of the present invention do not require the insertion multiple dissection tools to perform procedure. Nor do they require multiple tool exchanges. Accordingly, the procedure as a whole is far easier, and efficient that those previously known. As a result the stress on the patient is reduced.

Although only a few exemplary embodiments of this invention have been described in detail above, those skilled in the art will readily appreciate that many modifications are possible without materially departing from the novel teachings and advantages of this invention. Accordingly, all such modification are intended to be included within the scope of this invention as defined in the following claims.

What is claimed is:

1. A surgical instrument for dissecting a vessel in a patient, said surgical instrument comprising:
    a spoon retractor having a proximal end and a distal end, said spoon retractor defining a working space in the tissue of a patient;
    a dissecting element proximate and rigidly fastened to said spoon retractor for dissecting tissue from a vessel; and
    means for manipulating said spoon retractor near the vessel.

2. The surgical instrument according to claim 1, where said means for manipulating the spoon retractor near the vessel comprises:
    a shaft having a distal end and a proximal end, the distal end of the shaft connected to the proximal end of the spoon retractor, the shaft having a lumen in communication with the working space for insertion of an endoscope there through; and
    a handle connected to a proximal end of the shaft for manipulation of the spoon retractor connected thereto.

3. The surgical instrument according to claim 1, wherein the dissecting element comprises a wireform, the wireform comprising a left side rail and a right side rail rigidly connected to the spoon retractor at a proximal end of the wireform, said left and right side rails being connected to each other at a distal end of the wireform and dissecting tissue from the left and right surfaces of the vessel.

4. The surgical instrument according to claim 1, wherein the wireform projects upward in the direction of the spoon retractor, and forms a U-shape at the distal end of the wireform to facilitate placement of the vessel between the left and right side rails.

5. The surgical instrument according to claim 1, comprising a control for controlling the dissecting element, wherein said dissecting element movably connects to said spoon retractor and moves relative to said spoon retractor upon actuation of the control, to facilitate dissection of tissue from the vessel.

6. The surgical instrument according to claim 1, wherein said dissecting element comprising a movable arm having an extended portion and a shank, the movable arm being rotatable about an axis defined by the shank.

7. The surgical instrument according to claim 1, wherein the dissecting element comprises a flexible arm slidably retained in said spoon retractor, and movable between an extended position and a retracted position.

8. The surgical instrument according to claim 7, wherein a distal end of the flexible arm defines at least one curved portion, the curved portion further defining an arm which extends to an outer edge of the flexible arm and facilitating the dissection of tissue from the vessel.

9. The surgical instrument according to claim 8, wherein the flexible arm is prevented from entering the workspace by guide rails.

10. The surgical instrument according to claim 1, wherein the dissection element comprises a left curved edge and a right curved edge extending from a bottom edge, the left and right curved edges opposing each other, and surrounding a longitudinal axis of the spoon retractor.

11. A surgical instrument for dissecting a vessel in a patient, said surgial instrument comprising:
    a spoon retractor having a proximal end and a distal end, said spoon retractor defining a working space in the tissue of a patient;
    a dissecting element proximate to said spoon retractor for dissecting tissue from a vessel, said dissecting element comprising a flexible arm slidably retained in said spoon retractor, and movable between an extended position and a retracted position; and
    means for manipulating said spoon retractor near the vessel.

* * * * *